(12) United States Patent
    Wade

(10) Patent No.: US 10,172,613 B1
(45) Date of Patent: Jan. 8, 2019

(54) PRE-LOADED, DISPOSABLE, DYNAMIC COMPRESSION BONE STAPLE DELIVERY DEVICES AND METHODS

(71) Applicant: Dallen Medical, Inc., San Clemente, CA (US)

(72) Inventor: Russell W. Wade, Laguna Niguel, CA (US)

(73) Assignee: Dallen Medical, Inc., San Clemente, CA (US)

( * ) Notice: Subject to any disclaimer, the term of this patent is extended or adjusted under 35 U.S.C. 154(b) by 543 days.

(21) Appl. No.: 14/796,957

(22) Filed: Jul. 10, 2015

Related U.S. Application Data

(60) Provisional application No. 62/023,033, filed on Jul. 10, 2014.

(51) Int. Cl.
    *A61B 17/064* (2006.01)
    *A61B 17/068* (2006.01)

(52) U.S. Cl.
    CPC ...... *A61B 17/0682* (2013.01); *A61B 17/0642* (2013.01)

(58) Field of Classification Search
    CPC ..... A61B 17/10; A61B 17/115; B25C 5/0235; B25C 5/025; B25C 5/0285; B25C 5/0292; B25C 5/11; B25C 5/1617; B25C 5/162
    See application file for complete search history.

(56) References Cited

U.S. PATENT DOCUMENTS

| | | | | |
|---|---|---|---|---|
| 6,755,338 B2* | 6/2004 | Hahnen | ............ | A61B 17/07207 227/175.1 |
| 2005/0125018 A1* | 6/2005 | Galloway | ........ | A61B 17/32093 606/181 |
| 2012/0312225 A1* | 12/2012 | Branch | ................. | G01L 5/0052 116/203 |

* cited by examiner

*Primary Examiner* — Anu Ramana
(74) *Attorney, Agent, or Firm* — Schwegman Lundberg & Woessner, P.A.

(57) ABSTRACT

A device for deploying a staple into desired bone has a staple guide for retaining a bone staple and a spring-loaded plunger shaft having a distal end proximal to the bone staple, the plunger shaft being retained in a proximal orientation by a latch. Depressing an actuator releases the latch, so that the plunger shaft moves to its distal position, striking the staple and deploying the staple distally into a bone site. An additional method step, in the event that one wishes to deploy a differently sized staple, involves detaching the staple guide from the device and attaching a differently-sized staple guide to the device. In order to avoid inadvertent deployment of the staple, a safety cover may be provided, in which case a further method step involves removing a safety cover from the device prior to the depressing step.

10 Claims, 2 Drawing Sheets

PRE-LOADED, DISPOSABLE, DYNAMIC COMPRESSION BONE STAPLE DELIVERY DEVICES AND METHODS

This application claims the benefit under 35 U.S.C. 119(e) of the filing date of Provisional U.S. Application Ser. No. 62/023,033, entitled Pre-Loaded, Disposable, Dynamic Compression Bone Staple Delivery Device, filed on Jul. 10, 2014, which application expressly incorporated herein by reference, in its entirety.

This application is also related to U.S. Pat. No. 6,059,787 entitled Compression Bone Staple, Apparatus and Method, issued May 9, 2000, to U.S. Pat. No. 6,348,054 entitled Compression Bone Staple, Apparatus and Method, issued Feb. 19, 2002, to U.S. Pat. No. 6,783,531 entitled Compression Bone Staple, Apparatus and Method, issued Aug. 31, 2004, and to U.S. patent application Ser. No. 13/745,651, filed on Jan. 18, 2013, entitled Compression Bone Staple, Apparatus and Method, all of which are commonly assigned and expressly incorporated herein, by reference, in their entirety.

BACKGROUND OF THE INVENTION

In treating a bone fracture it is common practice to fasten one bone segment to the other so as to stabilize and immobilize them for the duration of the bone consolidation process. Thus there is the technique of internal fixation or direct mechanical fastening of the bone segments. Traditionally, fixation has been accomplished by variety of apparatus and techniques, the more common involving the use of metallic fastening devices such as screws, connector plates (secured to the bone by screws), pins and clips. These methods invariably involve the drilling of screw holes in the bone and the use of related equipment such as drill hole templates. In view of the limitations of the afore-mentioned methods, stapling has been looked to as a way to produce compression.

Compression bone staple delivery devices are known in the art. However, a pre-loaded, disposable, dynamic compression bone staple device would add additional valuable options for orthopedic surgeons.

SUMMARY OF THE INVENTION

A pre-loaded, disposable, dynamic compression bone staple delivery system is disclosed for providing additional options for orthopedic surgeons.

More particularly, there is provided a compression bone staple delivery system which comprises a guide for retaining a staple thereon, and a shaft proximal to the guide, movable between proximal and distal orientations and positioned so that a distal end of the shaft impacts a staple retained on the guide for deploying the staple distally into a desired bone site when the shaft is moved from a proximal orientation to a distal orientation. A spring is provided for biasing the shaft toward its distal orientation. A latch is disposed for restraining the shaft in a proximal orientation. A latch release is actuatable to move the latch to a non-restraining orientation so that the shaft moves to its distal orientation, thereby deploying the staple disposed on the guide.

A housing contains the shaft, spring, latch, and latch release, as well as securing the guide in position distal to the shaft. The housing comprises a first housing portion and a second housing portion which are securable together to form the housing. A circumferential groove is disposed on the shaft for engagement with the latch.

The spring comprises a compression spring captured between a proximal end of the shaft and a proximal end of the housing in a compressed orientation so that energy is stored for release to drive the shaft distally when the latch is disengaged from the shaft by the latch release. The latch comprises a pawl for engagement with the groove on the shaft, a rigid frame joined to the pawl, and a compression spring for biasing the latch into an engaged orientation with the shaft. In the disclosed embodiment, the latch release comprises a button disposed on the housing which is connected to the latch frame and, when engaged, releases force applied by the latch compression spring on the pawl.

A safety cover is provided for preventing inadvertent actuation of the latch release, the safety cover comprising a safety tab for disposition between the button and the housing to prevent the button from moving downwardly when depressed. The safety cover is removable to permit release of the latch, and is preferably translucent.

The staple guide, in a disclosed embodiment, comprises a distal portion having a concave recess for receiving a bridge of a staple and a proximal portion for securing the staple guide to a distal end of the housing. A plurality of staple guides of different sizes may be supplied, adapted for use with corresponding staples of different sizes, the guides being interchangeble in the system by removing a first guide and installing a second guide.

In another aspect of the invention, there is disclosed a method of deploying a bone staple into a desired bone site. The method comprises a step of locating a bone staple delivery device adjacent to a desired bone site. The device has a staple guide for retaining a bone staple thereon with the bone staple disposed at a distal end of the device, directly adjacent to the bone site. The device further comprises a spring-loaded plunger shaft having a distal end proximal to the bone staple, the plunger shaft being retained in a proximal position by a latch. A further step of the method is the depressing of an actuator to release the latch, so that the plunger shaft moves to its distal position, striking the staple and deploying the staple distally into the bone site.

An additional method step, in the event that one wishes to deploy a differently sized staple, involves detaching the staple guide from the device and attaching a differently-sized staple guide thereto.

In order to avoid inadvertent deployment of the staple, a safety cover may be provided, in which case a further method step comprises removing a safety cover from the device prior to the depressing step.

The invention, together with additional features and advantages thereof, may best be understood by reference to the following description taken in conjunction with the accompanying illustrative drawings.

DESCRIPTION OF THE PREFERRED EMBODIMENT

Figure 1:
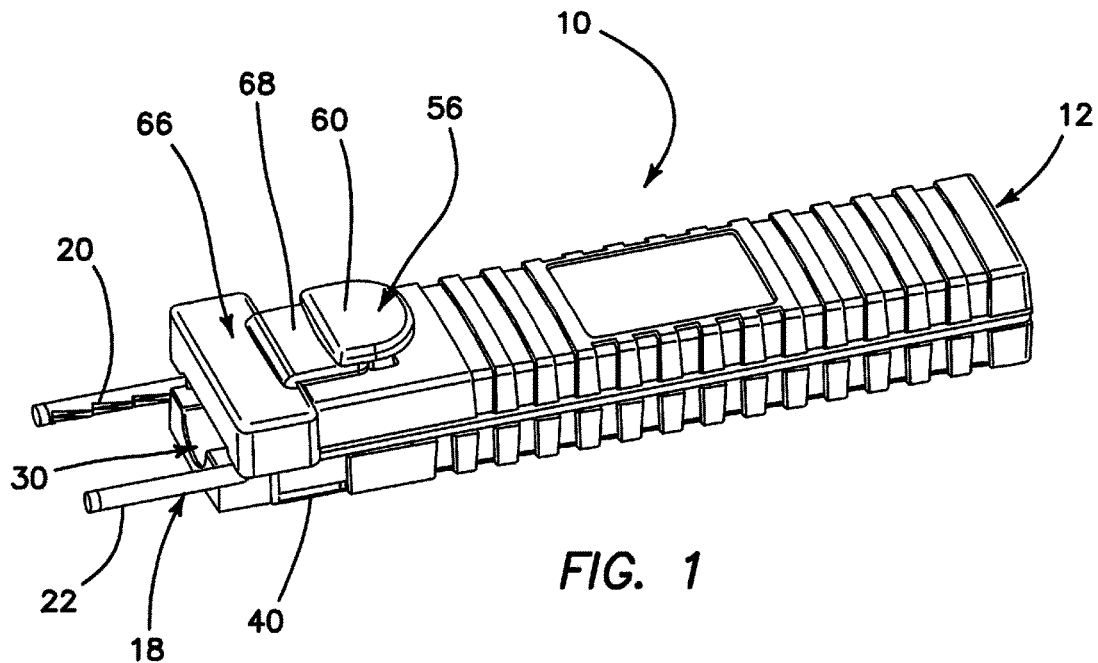
FIG. 1 is a top isometric view of a compression bone staple delivery device constructed in accordance with the principles of the present invention, with a staple and safety retainer in place.
Figure 2:
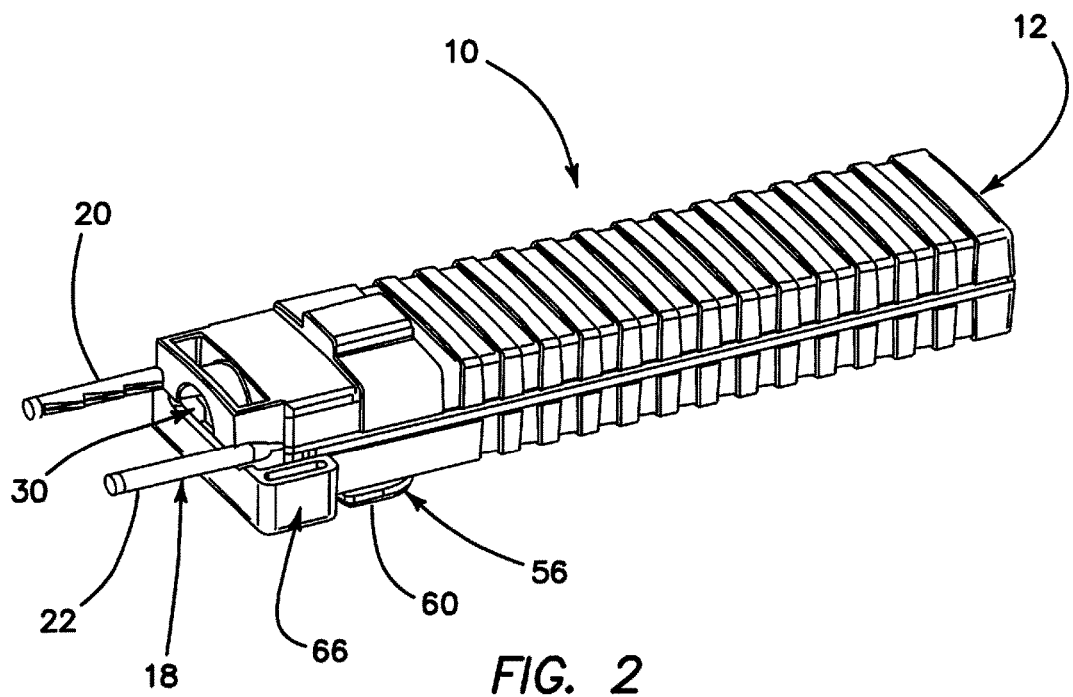
FIG. 2 is a bottom isometric view of the compression bone staple delivery device of FIG. 1.
Figure 3:
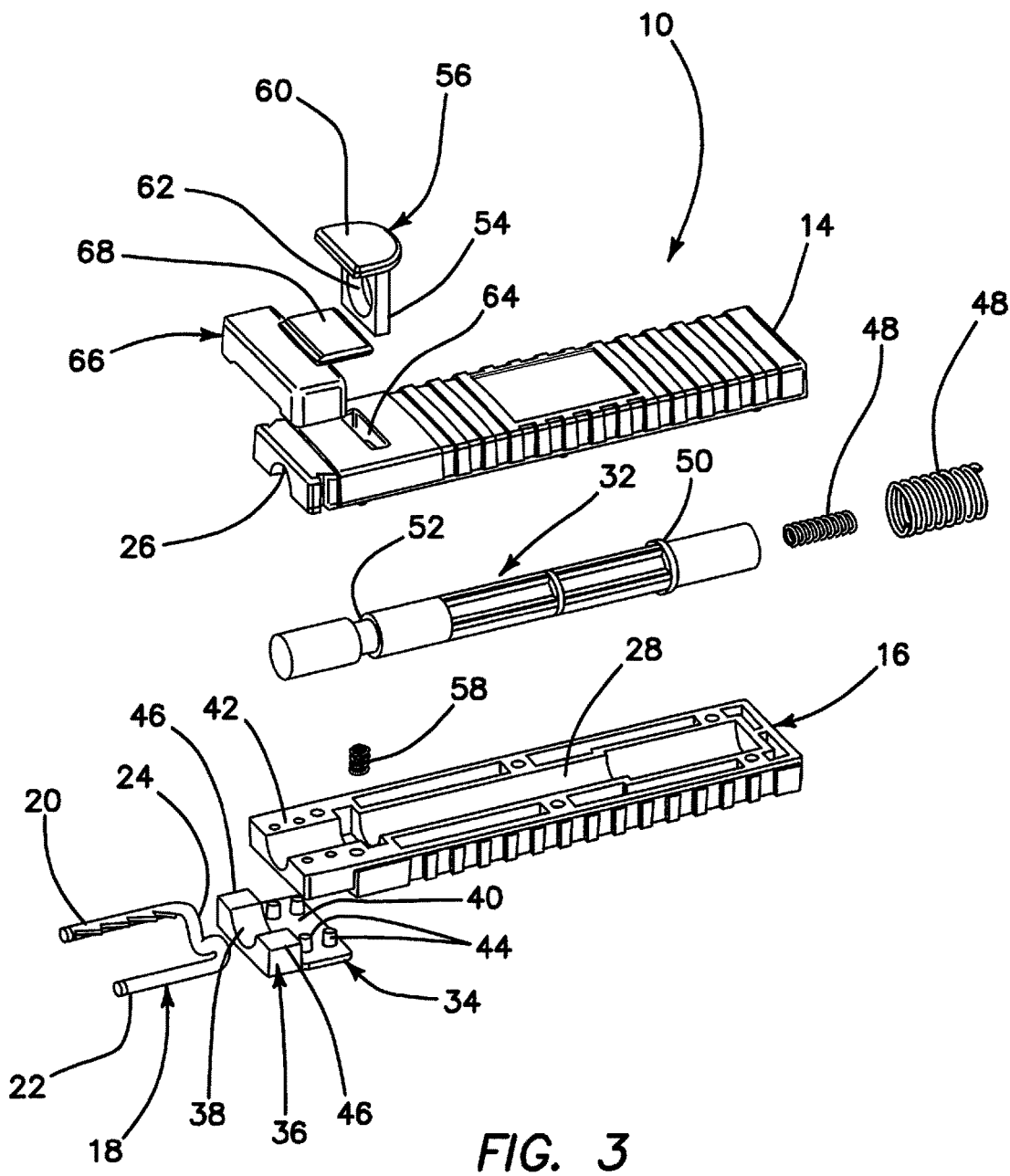
FIG. 3 is an exploded isometric view of the device shown in FIGS. 1 and 2.

Referring more particularly to the drawings, there is shown in FIGS. 1-3 a compression bone staple delivery device 10 constructed in accordance with one embodiment of the present invention. The device 10 comprises a housing 12 formed of a first housing portion 14 and a second housing portion 16 (FIG. 3) which may be secured together to assemble the housing 12 as shown in FIGS. 1-2. The housing portions 14, 16, when assembled, form a grasping and containing mechanism for the delivery device 10, and are shaped in such a way as to provide a visual clue to the orientation of a staple 18 disposed therein.

The staple 18 may be constructed as is disclosed in any of commonly assigned U.S. Pat. Nos. 6,059,787, 6,348,054, or 6,783,531, or in U.S. patent application Ser. No. 13/745,651, for example, all of which have already been expressly incorporated herein by reference, and may comprise a pair of legs 20, 22, respectively, joined by a bridge 24. The staple 18 will not be further described herein, because the purpose of this application is to describe and claim an inventive staple delivery device 10, and it is suitable for use with any bone staple.

As shown best in FIG. 3, the housing 12 includes complementary lengthwise recesses 26 and 28, in each of the housing portions 14 and 16, respectively, so that when the housing 12 is assembled, a lengthwise shaft opening 30 is formed to accommodate a shaft 32 and associated elements therein, as will be described further hereinbelow. The shaft 32 functions for striking and delivering a staple.

The device 10 further comprises a staple guide 34, for receiving and retaining a staple 18 thereon, and for guiding the staple 18 into pre-drilled holes in bone. The staple guide 34 includes a distal portion 36 having a concave recess 38 for receiving the bridge 24 of a staple 18, as shown in FIG. 3, and a proximal portion 40 for attaching the staple guide 34 to a distal end 42 of the second housing portion 16 using snap-on lugs 44 or other suitable fasteners.

The staple guide 34 has guide features 46, which may comprise channels matching the configuration of legs 20, 22, included on the distal portion 36 thereof, that allow a staple 18 to slide in place during assembly, and to slide off when deployed. The concave recess 38 provides clearance from the staple 18 and shaft 32, and counter-sunk holes on the lower surface of the distal end 42 of the second housing portion allow for flush mounting of the staple guide, inserting the lugs 44 into the counter-sunk holes, during assembly. The device 10 can be manufactured to accommodate a variety of common staples by installing different staple guides 34 which are each configured specifically for use with one particular size staple. Small staples will have matching small guides 34 and large staples will have matching large guides.

As noted above, a shaft 32, comprising a plunger shaft, is disposed in the lengthwise shaft opening 30 of the device 10. The purpose of the plunger shaft 32 is to drive the staple 18 into bone, at a desired time. Accordingly, a compression spring 48 is disposed at a proximal end of the shaft 32, which has a hole for the compression spring 48 at its proximal end, for attaching the compression spring 48 thereto, as well as a raised rib 50 to provide a method for stopping forward motion of the shaft and retaining it within the housing embodiment. A distal end of the shaft 32 includes a groove 52 to interface with a pawl 54 of a latch 56 to retain the shaft 32 under compression, due to the force applied by compression spring 48, until the latch 56 is released. The compression spring 48 has sufficient compressive force to drive the shaft 32, which causes a distal end of the shaft 32 to strike the staple into pre-drilled holes in bone.

A compression spring 58 is provided for the latch 56, for the purpose of providing upward force on the latch prior to release, to ensure a positive release at the desired time by pressing a contoured button 60 using a finger. The compression spring 58 for the latch 56 has sufficient force to keep the pawl 54 of the latch 56 engaged in the shaft groove 52 until intentionally released and compliant enough to allow easy activation when force is applied with a finger or otherwise.

As noted above, the latch 56 functions to retain and release the spring-loaded shaft 32 to deliver a staple, and has an offset hole 62 eccentric to and above the shaft on a rigid frame perpendicular to the shaft, a rigid frame sufficient in strength to hold load from the spring-loaded shaft until released, and sides that interlock with the housing, as the latch frame extends through aperture 64 in the housing, to act as guides when the latch is pressed with a finger.

The ribs formed by the walls defining the aperture 64 assist in grasping and placement of the release latch 56 to allow for a single-handed use of the device. Internal features of the housings provide for capture of the shaft 32, compression springs 48 and 58, latch 56, and mounting features for the guide 34 and a safety cover 66.

The safety cover 66, to prevent inadvertent activation of a staple 18, has guide ribs that match the housing and allow it to be pressed and snapped into position, as shown. When in place, as shown in FIG. 1, a safety tab 68 is interposed between the top of the first housing portion 14 and the button 60, thereby preventing actuation of the latch 56 while the safety cover 66 is in place. The cover 66 is also preferably translucent, thereby allowing visual verification of the cover, shaft, and staple position.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A compression bone staple delivery system, comprising:
   a staple guide for retaining a staple thereon;
   a shaft proximal to the staple guide, movable between proximal and distal orientations and positioned so that a distal end of the shaft impacts a staple retained on the staple guide for deploying the staple distally into a desired bone site when the shaft is moved from a proximal orientation to a distal orientation;
   a spring for biasing the shaft toward its distal orientation;
   a latch for restraining the shaft in a proximal orientation;
   a latch release, the latch release being actuatable to move the latch to a non-restraining orientation so that the shaft moves to its distal orientation, thereby deploying the staple disposed on the staple guide; and
   a housing for containing the shaft, spring, latch, and latch release, and for securing the staple guide in position distal to the shaft;
   wherein the staple guide comprises a distal portion having a concave surface depression for receiving a bridge of a staple and a proximal portion for securing the staple guide to a distal end of the housing.

2. The system as recited in claim 1, wherein the housing comprises a first housing portion and a second housing portion which are securable together to form the housing.

3. The system as recited in claim 1, and further comprising a circumferential groove on said shaft for engagement with said latch.

4. The system as recited in claim 3, wherein the latch comprises a pawl for engagement with the groove on the shaft, a rigid frame joined to the pawl, and a second compression spring for biasing the latch into an engaged orientation with the shaft.

5. The system as recited in claim 1, wherein the spring comprises a compression spring captured between a proximal end of the shaft and a proximal end of the housing in a compressed orientation so that energy is stored for release to drive the shaft distally when the latch is disengaged from the shaft by the latch release.

6. The system as recited in claim 1, wherein the latch release comprises a button disposed on said housing which is connected to the latch frame and, when engaged, releases force applied by the latch compression spring on the pawl.

7. The system as recited in claim 6, and further comprising a safety cover for preventing inadvertent actuation of the latch release, the safety cover comprising a safety tab for disposition between the button and the housing to prevent the button from moving downwardly when depressed.

8. The system as recited in claim 7, wherein the safety cover is removable to permit release of the latch.

9. The system as recited in claim 7, wherein the safety cover is translucent.

10. The system as recited in claim 1, and further comprising a plurality of staple guides of different sizes, adapted for use with corresponding staples of different sizes, the staple guides being interchangeble in the system by removing one staple guide and installing another staple guide.

* * * * *